| United States Patent [19] | [11] | 4,343,734 |
| Lian et al. | [45] | Aug. 10, 1982 |

[54] PROTEIN DIAGNOSTIC FOR ATHEROSCLEROSIS

[75] Inventors: Jane B. Lian, N. Weymouth; Robert J. Levy, Newton; Paul M. Gallop, Chestnut Hill, all of Mass.

[73] Assignee: The Children's Hospital Medical Center, Boston, Mass.

[21] Appl. No.: 111,115

[22] Filed: Jan. 10, 1980

[51] Int. Cl.³ ............... A61K 35/14; A61K 37/02; A61K 49/02; C07G 7/00
[52] U.S. Cl. ............... 260/112 B; 260/112 R; 424/1; 424/3; 424/85; 424/101
[58] Field of Search ............... 260/112 R, 112 B; 424/101, 85

[56] References Cited

PUBLICATIONS

Biochem. Biophys. Res. Comm. 73, 349–355, (1976), Lian et al.
Circulation (Abstract, Supp. III) 56,167 (1977), Fallon et al.
Biochem. 18, 899–904, (1979), Discipio et al., No. 5, Mar. 6, 1979.

*Primary Examiner*—Howard E. Schain

[57] ABSTRACT

Compositions and processes featuring, in one aspect, a process of purifying a protein diagnostic for atherosclerosis comprising separating out of primate and human atherosclerotic tissue a Gla-containing protein of molecular weight of about 80,000.

16 Claims, 4 Drawing Figures

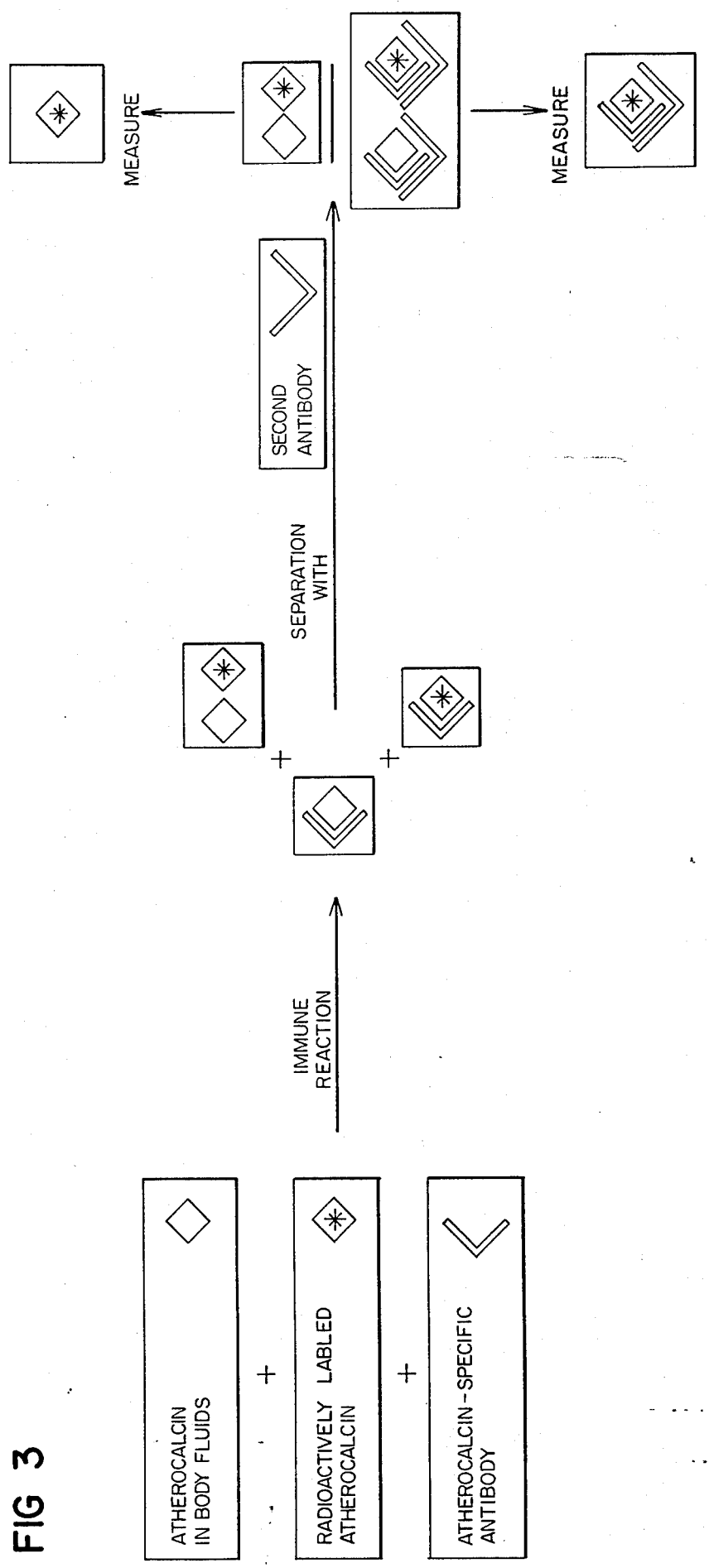

PROTEIN DIAGNOSTIC FOR ATHEROSCLEROSIS

The invention described herein was made in the course of work under a grant or award from the Department of Health and Human Services.

BACKGROUND OF THE INVENTION

This invention relates to proteins diagnostic for atherosclerosis and other pathological states involving vascular calcification; e.g., arteriosclerosis, valve calcification, and prosthesis calcification.

Later stages in the sequelae of atherosclerosis are characterized by the presence of calcified plaques. The amino acid Gamma-carboxyglutamic acid (Gla), which is dependent upon vitamin K for its synthesis and is known to bind calcium, has been studied in connection with such plaques.

Lian et al. (1976) Biochem. Biophys. Res. Comm. 73, 349-355 describes work demonstrating the presence of Gla in the calcified atheromatous plaques in the aortas of patients suffering from advanced atherosclerosis. Uncalcified aorta samples from the same patients contained no Gla.

Fallon et al. (1977) Circulation (Abstract, Supp. III) 56, 167 describes the isolation, from calcified human cardiac valves and aortas, of a polypeptide which contains Gla, and which has a molecular weight of about 2,000. Tissue homogenates were extracted with EDTA and the extracts were desalted, freeze dried, and chromatographed on P-6 resin.

Gla is also found in various circulating proteins not associated with atherosclerosis. Examples are prothrombin, clotting factors VII, IX, and X, Protein C, and Protein S, described in DiScipio et al. (1979) Biochem. 18, 899-904.

SUMMARY OF THE INVENTION

Our invention provides a purified Gla-containing protein whose association with atherosclerotic tissue makes it useful in the diagnosis of atherosclerosis.

In one aspect, the invention features the purified protein (hereinafter referred to as "atherocalcin") and the methods for its purification from human and primate atheroscelerotic tissue on the basis of its physical and chemical properties, which include, in preferred embodiments, a molecular weight of about 80,000, an isoelectric point of between about 4.16 and 4.30, and a particular amino acid composition.

In another aspect, the invention features an antibody specific for atherocalcin.

In yet another aspect, the invention features using the new antibody in a radioimmunoassay procedure in which an unknown quantity of atherocalcin in a sample competes for antibody with labelled atherocalcin; both complexed and uncompleted label are inversely proportional to the atherocalcin content of the sample.

In yet another aspect, the invention features making an immunofluorescent histological stain specific for atherocalcin by conjugating the atherocalcin-specific antibody with a fluorescent compound and using the stain to determine the presence of atherocalcin in tissue samples.

Because atherocalcin is associated with atherosclerotic tissues, the measurement of atherocalcin levels in tissue and body fluids can serve as a diagnostic index or clinical parameter of the progressive calcification characteristic of the sequelae of the atherosclerotic state.

DESCRIPTION OF THE PREFERRED EMBODIMENTS

We turn now to the description of the preferred embodiments, after first briefly describing the drawings.

Drawings

FIG. 1 is a gel filtration chromatography profile of polypeptide extracted from atherosclerotic plaques. Elution volume, inversely proportional to molecular weight, is measured on the horizontal axis, and absorbance of UV light of 280 nm wavelength, a measure of the total polypeptide content of each fraction, is measured on the vertical axis. The percentage of the total Gla content of each fraction, as measured by amino acid analysis, is given under each peak.

FIG. 3 is a block diagram of the radioimmunoassay procedure employing atherocalcin-specific antibody.

PURIFICATION OF ATHEROCALCIN

To obtain purified atherocalcin, human atherosclerotic aortas were obtained at autopsy and plaques exhibiting calcification were dissected out over ice. (Normal aortas were also obtained and analyzed as controls). Plaques were rinsed with cold saline to remove blood, freeze dried, and delipidated with 3:1 (v/v) chloroform methanol for 24 hours at 4°. The residue was dried under vacuum, rotary evaporated, and milled to a coarse powder under liquid nitrogen.

Polypeptides were then extracted by the following procedure. The residue was delipidated a second time, then extracted with 50% aqueous pyridine for 24 hours at 4° C. The powdered extract was then washed with distilled water, freeze dried, extensively dialyzed against distilled water, and again freeze dried. The solid residue was demineralized in 0.5 M citric acid at 4° C., washed, freeze dried, dialyzed as described above, and again freeze dried. Finally, the residue was extracted in 0.25 M dithiothreitol in 20 mM imidazole (pH 8.0) for 24 hours at 4° C. The extract was extensively dialyzed against distilled water and freeze dried.

Figure 1:
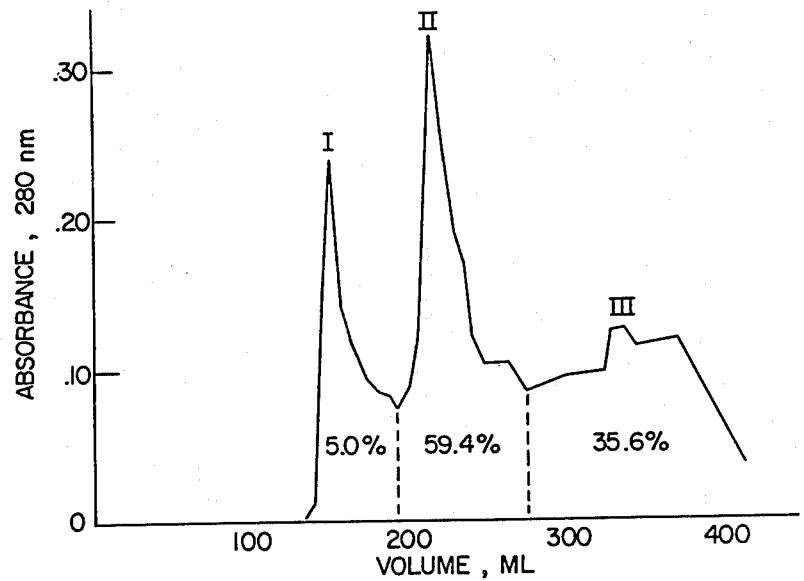

There is shown in FIG. 1 the gel filtration chromatography profile of the polypeptide extract. The extract was chromatographed on Sephacryl S-200 Superfine columns (2.5×100 cm) eluting with 0.1 M ammonium acetate (pH 7.1) in 0.7 mM dithiothreitol at a flow rate of 8.0 ml/hr. Automated amino acid analysis was performed on 2 N KOH hydrolysates of each of the three resulting fractions to determine the Gla content of each, by the method of Hauschka (1977) Analyt. Biochem 80, 212-223. Gla content was confirmed by 6 N NCl decarboxylation of the hydrolysates, which converted the putative Gla to glutamic acid, followed by automated amino acid analysis as described above. FIG. 1 shows two Gla-rich peaks: peak III, a polypeptide fraction which has a molecular weight below 6,000 and thus is generally not called protein, and peak II, a protein fraction which has a molecular weight over 6,000. The peak II fraction contained partially purified atherocalcin.

Figure 2:
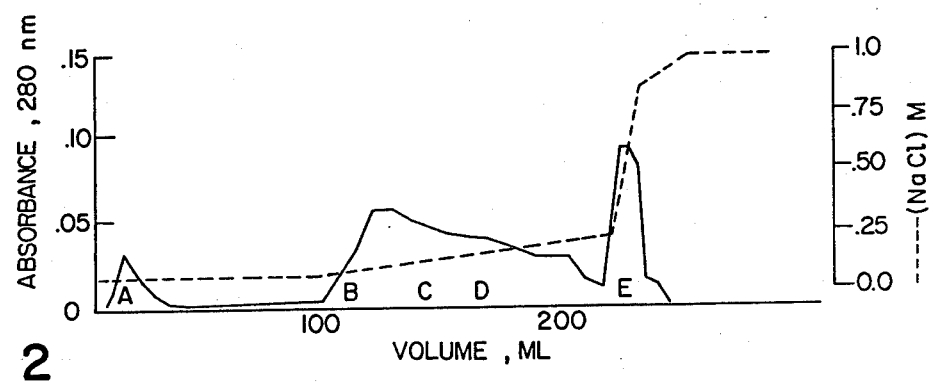
FIG. 2 is an ion exchange chromatography profile of peak II of FIG. 1. The horizontal axis measures elution volume, one vertical axis measures 280 nm absorbance, and the other vertical axis measures the NaCl gradient used.

There is shown in FIG. 2 an ion exchange chromatography profile of the peak II fraction of FIG. 1. To separate this fraction into fractions having different amino acid compositions, it was chromatographed using a DEAE cellulose column (1.5×25 cm) run at 60 ml/hr. with a buffer containing 20 mM imadazole, 2 mM EDTA, 20 mM $CaCl_2$ at pH 7.0 with an NaCl gradient as shown in FIG. 2. The resulting fractions were then assayed for Gla content as described above. The assay showed that peak D of FIG. 2 was the only Gla-containing protein fraction; this fraction, when re-chromatographed on the DEAE column, constituted purified atherocalcin.

The molecular weight of atherocalcin was determined to be about 80,000 by subjecting samples to SDS disc-gel electrophoresis at 14° C. with 15% acrylamide vertical slab gels using the procedure of Neville et al. (1971) J. Biol. Chem. 246, 6339–6346. A single band was observed, indicating purity. Establishment of the molecular weight makes possible the use of separation methods such as electrophoresis, gel filtration, and ultracentrifugation in the purification of atherocalcin from atherosclerotic tissue.

The isoelectric point of atherocalcin was determined to be between about 4.16–4.30 by subjecting samples to isoelectric focusing at 2° C. on a horizontal slab isoelectric focusing apparatus, using 4% acrylamide gels and an ampholyte mixture (pH 4–6), while maintaining constant power at 8.0 watts for three hours. The electrofocusing gels were stained with Coomassie blue by the method of Righetti et al. (1974) J. Chromatogr. 98, 271–318. Establishment of the isoelectric point makes possible the use of isoelectric focusing in the purification of atherocalcin from atherosclerotic tissue. Isoelectric focusing may also be performed prior to or following the use of one or more of the separation methods based on molecular weight.

Automated amino acid analysis was performed on 2 N KOH hydrolystates of atherocalcin, by the method described above. The amino acid residue composition thus established is shown in Table 1 below. (Of course, sample to sample variation, as well as variations in methods and sample purity, can result in values differing slightly from those of Table I.)

TABLE I

| Amino Acid | Residues per 1000 Amino Acids |
|---|---|
| Asp | 153 |
| Thr | 62 |
| Ser | 69 |
| Glu | 169 |
| Pro | 50 |
| Gly | 59 |
| Ala | 68 |
| Cys | 19 |
| Val | 63 |
| Met | 10 |
| Ile | 38 |
| Leu | 68 |
| Tyr | 17 |
| Phe | 36 |
| His | 21 |
| Lys | 50 |
| Arg | 36 |
| Gla | 19 |

An antibody specific for atherocalcin and having diagnostic uses can be produced by immunizing laboratory mammals with purified atherocalcin suspended in whole Freunds adjuvant having a concentration of 2 mg/ml. Blood is harvested 3 and 6 weeks after immunization, and the serum containing the antibody is separated out of the blood using conventional techniques.

Radioimmunoassay

There is shown in FIG. 3 a block diagram of the radioimmunoassay procedure which can be used to assay a body fluid such as blood or urine for atherocalcin. The method is a competitive binding assay of the type generally described in Ranson et al. *Practical Competitive Binding Assays* (St. Louis 1967). Purified atherocalcin can be radioactively labelled with Iodine 125 by the chloramine-T method described in *Methods in Immunology and Immunochemistry* (Academic Press 1967). The labelled atherocalcin can be mixed with antibody and the body fluid sample to be assayed, so that antibody complexes with competing labelled and unlabelled atherocalcin. Complexed atherocalcin/antibody can then be separated out generally by the procedure described in relation to human growth hormone in *Practical Binding Assays, op cit*, pp. 78–79. A commercially available antibody specific for the serum of the animal species used to make the atherocalcin-specific antibody can be mixed with the protein and antibody mixture described above, precipitating labelled and unlabelled complexed atherocalcin/antibody. The radioactivity of the precipitate or of uncomplexed protein can be determined using conventional means such as a scintillation counter. The fraction of labelled atherocalcin which is bound to antibody is inversely proportional to the atherocalcin content of the sample.

Immunofluorescent Stain

Figure 4:
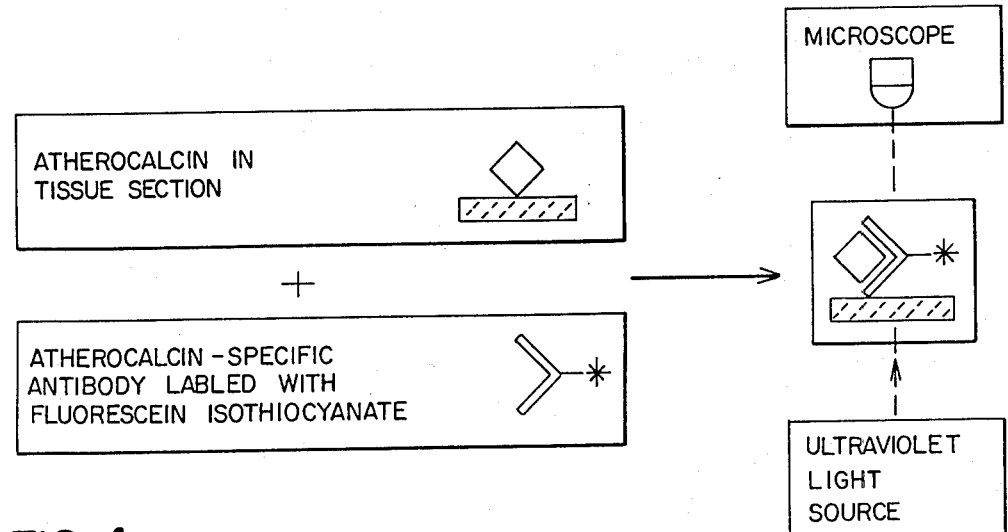
FIG. 4 is a block diagram of the procedure for making and using the fluorescent stain specific for atherocalcin.

There is shown in FIG. 4 a block diagram of a method of making and using an immunofluorescent stain which can be useful in determining the atherocalcin content of tissues. The stain can be produced by conjugating the atherocalcin-specific antibody described above with fluorescein isothiocyanate. Frozen section tissue samples can be stained and examined using conventional methods described in, e.g., Culling, *Handbook of Histopathological Techniques* (London 1966). Fluorescent tissues or tissue areas are those containing atherocalcin.

Other Embodiments

Other embodiments, including other modes of atherocalcin extraction employing EDTA (Levy et al. (1979) BBRC 91, 41), cold dilute HCl, cold acetic acid, and other organic acids, are within the following claims.

We claim:

1. A process of purifying a protein diagnostic for atherosclerosis, said protein having an amino residue composition as set forth in Table I, being derived from primate atherosclerotic tissue, having a molecular weight of about 80,000 as determined by SDS disc-gel electrophoresis at 14° C. with 15% acrylamide vertical slab gels, and having an isoelectric point between 4.16 and 4.30 as determined by isoelectric focusing at 2° C. on a horizontal slab isoelectric focusing apparatus using 4% acrylamide gels and an ampholyte mixture, at pH 4–6, while maintaining constant power at 8.0 watts for three hours, said process comprising the steps of
obtaining primate atherosclerotic tissue, and
separating out of said tissue a Gla-containing protein having a molecular weight of about 80,000.

2. The process of claim 1 wherein said separating is carried out by electrophoresis.

3. The process of claim 1 wherein said separating is carried out by ultracentrifugation.

4. The process of claim 1 wherein said separating is carried out by gel filtration.

5. The process of purifying a protein diagnostic for atherosclerosis, said protein having an amino residue composition as set forth in Table I, being derived from primate atherosclerotic tissue, having a molecular weight of about 80,000 as determined by SDS disc-gel electrophoresis at 14° C. with 15% acrylamide vertical slab gels, and having an isoelectric point between 4.16 and 4.30 as determined by isoelectric focusing at 2° C. on a horizontal slab isoelectric focusing apparatus using 4% acrylamide gels and an ampholyte mixture, at pH 4-6, while maintaining constant power at 8.0 watts for three hours, said process comprising the steps of
obtaining primate atherosclerotic tissue, and
separating out of said tissue a Gla-containing protein having an isoelectric point between about 4.16 and 4.30.

6. The process of claim 5 wherein said separating is carried out by isoelectric focusing.

7. The process of claim 1, further comprising the step of separating out of said tissue a Gla-containing protein having an isoelectric point between about 4.16 and 4.30.

8. The process of claim 7 wherein said separating comprises the steps of
removing blood from said tissue,
removing lipids from said tissue,
extracting the polypeptide fraction from said tissue,
performing gel filtration on said polypeptide fraction to increase the concentration of protein of molecular weight of about 80,000, and
performing isoelectric focussing on said polypeptide fraction to increase the concentration of polypeptides of isoelectric point between about 4.16–4.30.

9. The process of claim 8 wherein said extracting of said polypeptide fraction is carried out by reacting said tissue with aqueous pyridine.

10. The process of claim 8 wherein said extracting of said polypeptide fraction is carried out by reacting said tissue with EDTA.

11. A process for purifying a protein diagonstic for atherosclerosis, said protein having an amino residue composition as set forth in Table I, being derived from primate atherosclerotic tissue, having a molecular weight of about 80,000 as determined by SDS disc-gel electrophoresis at 14° C. with 15% acrylamide vertical slab gels, and having an isoelectric point between 4.16 and 4.30 as determined by isoelectric focusing at 2° C. on a horizontal slab isoelectric focusing apparatus using 4% acrylamide gels and an ampholyte mixture, at pH 4-6, while maintaining constant power at 8.0 watts for three hours, said process comprising the steps of
obtaining primate atherosclerotic tissue, and
separating out of said tissue a protein having an amino acid residue composition as set forth in Table I.

12. The process of any one of claims 1 to 11 wherein said primate atherosclerotic tissue is human atherosclerotic tissue.

13. A purified protein diagnostic for atherosclerosis purified by the process of any one of claims 1 to 10.

14. A purified protein diagnostic for atherosclerosis, said protein having an amino residue composition as set forth in Table I, being derived from primate atherosclerotic tissue, having a molecular weight of about 80,000 as determined by SDS disc-gel electrophoresis at 14° C. with 15% acrylamide vertical slab gels, and having an isoelectric point between 4.16 and 4.30 as determined by isoelectric focusing at 2° C. on a horizontal slab isoelectric focusing apparatus using 4% acrylamide gels and an ampholyte mixture, at pH 4-6, while maintaining constant power at 8.0 watts for three hours.

15. The process of making an antibody specific for a protein diagnostic for atherosclerosis comprising the steps of
injecting into a mammal a purified protein diagnostic for atherosclerosis, said protein having an amino residue composition as set forth in Table I, being derived from primate atherosclerotic tissue, having a molecular weight of about 80,000 as determined by SDS disc-gel electrophoresis at 14° C. with 15% acrylamide vertical slab gels, and having an isoelectric point between 4.16 and 4.30 as determined by isoelectric focusing at 2° C. on a horizontal slab isoelectric focusing apparatus using 4% acrylamide gels and an ampholyte mixture, at pH 4-6, while maintaining constant power at 8.0 watts for three hours, thereby to stimulate said mammal to produce said antibody, and
removing from said mammal blood containing said antibody.

16. The antibody made by the process of claim 15.

* * * * *